United States Patent [19]

Komura et al.

[11] 4,397,944

[45] Aug. 9, 1983

[54] COMPOSITIONS FOR DIAGNOSIS OF DENTAL CARIES ACTIVITY

[75] Inventors: Tamotsu Komura, Nara; Masayoshi Tsunekawa, Toyonaka; Sadayuki Yuhda, Suita, all of Japan

[73] Assignee: Sankin Industry Co., Ltd., Osaka, Japan

[21] Appl. No.: 221,512

[22] Filed: Dec. 30, 1980

[30] Foreign Application Priority Data

Dec. 31, 1979 [JP] Japan ................. 55-171485

[51] Int. Cl.³ .............. C12Q 1/00; C12Q 1/04; G01N 31/16; G01N 33/48
[52] U.S. Cl. ......................... 435/4; 424/7.1; 424/49; 424/78; 424/83; 435/34; 436/163
[58] Field of Search ............ 424/7, 49, 78, 83, 7.1; 435/4, 34; 436/163

[56] References Cited

U.S. PATENT DOCUMENTS

| | | | |
|---|---|---|---|
| 1,112,180 | 9/1914 | Westenfelter | 424/7 X |
| 3,746,624 | 7/1973 | Hoerman | 424/7 X |
| 4,050,895 | 9/1977 | Hardy | 424/12 X |

FOREIGN PATENT DOCUMENTS

| | | | |
|---|---|---|---|
| 51-38427 | 3/1976 | Japan | 424/7 |
| 51-38428 | 3/1976 | Japan | 424/7 |
| 54-47700 | 4/1979 | Japan . | |

OTHER PUBLICATIONS

Hardwick, British Dental J., vol. 108, No. 7, 1960, pp. 255-259.
Sanitology in Mouth Cavity, Gifu Dental College, 1974, pp. 41–42.
Fusayama, J. Dent. Res., May–Jun., 1972, p. 866.

*Primary Examiner*—Anna P. Fagelson
*Attorney, Agent, or Firm*—Oblon, Fisher, Spivak, McClelland & Maier

[57] ABSTRACT

Compositions capable of evaluating dental caries activity by making use of color reaction, which are composed of an aqueous solution containing coloring agents and water-soluble substances that are to produce an osmotic pressure higher than the physiological one on the cell membrane of cariogenic bacteria but free from any buffer action by themselves. Upon introducing dental plaque of a dental caries patient into this solution and thus measuring activity of the sordes by means of color reaction, it is possible to evaluate readily the status praesens of dental caries and its activity without any cultivation of cariogenic bacteria being required.

6 Claims, 4 Drawing Figures

COMPOSITIONS FOR DIAGNOSIS OF DENTAL CARIES ACTIVITY

BACKGROUND OF THE INVENTION

1. Field of the Invention

This invention relates to compositions for diagnosis of dental caries activity, more particularly to compositions capable of evaluating instantly the status praesens of dental caries (decayed tooth) and its activity by having recourse to dental plaque collected from the dental caries patient's oral cavity. According to this invention, it is possible above all to evaluate instantly the status praesens of the patient's dental caries and its activity by means of color reaction like Schneider's test without any cultivation of cariogenic bacteria being required.

2. Description of the Prior Art

It is said that three important factors, e.g. cariogenic bacteria, sugar and dentine, participate in genesis and development of dental caries (Ind. Dent. J., 12, 443 (1962)). In consequence, a synthetic judgement as to all of these factors should be brought about in order to have the full knowledge of the genesis and development of dental caries, but it is difficult to make simultaneous measurements of all these factors. Under the circumstances, different test methods have been inquired into whereby the status praesens of dental caries can be objectively evaluated by observing the condition of cariogenic bacteria in dental plaque for reason that this condition is highly correlated with dental caries. Snyder's test, salivary lactobacillus count test, dental enamel dissolution test, salivary acid fermentation test, salivary buffering power test, etc. are the typical ones among them. However, these test methods have offered some problems in that troublesome operations are involved in spite of the results to be obtained being not consistent, that the instruments to be used are complicated and moreover that it takes a long time for cultivation of cariogenic bacteria. With the use of these methods, therefore, examination of the oral cavity still remains indispensable for judging of the status praesens of dental caries.

The authors of this invention, having taken the situation as stated above into account, have pursued their researches with a view to developing any method for evaluating the status praesens of dental caries that could take the place of examination of the oral cavity, and have previously proposed a method for test of dental caries activity (Public Disclosure of Patent Application No. 1589/75). This method consists in placing dental plaque collected from the oral cavity in an aqueous solution containing a carbon source (saccharose), a nitrogen source (Tryptose (an amino acid composite prepared by Difco in U.S.A.), etc.) and coloring agents as well as an agent inhibiting proliferation of sundry germs not related with dental caries and then, after cultivation of the bacteria for a given duration, in deciding on dental caries activity on the basis of coloration of the culture solution. Though this method is certinaly an excellent one in matter of simplicity of operation and accuracy in evaluation, yet it is a method which essentially requires bacterial cultivation and therefore certain time until any judgement has been given.

SUMMARY OF THE INVENTION

The object of this invention which has been achieved by paying attention to these circumstances is to offer any compositions for diagnosis of dental caries activity capable of accurately evaluating the status praesens of dental caries and its activity toward future development by means of color reaction. Another object of the invention lies in making available any compositions which should enable an instant evaluation of the degree of dental caries by using dental plaque collected from the dental caries patient's oral cavity and without bacterial cultivation. Further objects of the invention will be clarified by the description in the following lines.

All of the said objects have been attained by adopting the method described hereunder.

It may be summarized that the essential point of this invention consists in combining some coloring agents exhibiting different colors at pH in the range comprised between 7.5-5.0 with an aqueous solution containing water-soluble substances which can produce an osmotic pressure higher than the physiological one on the cell membrane of cariogenic bacteria and yet are free from any buffer action by themselves.

Figure 1:
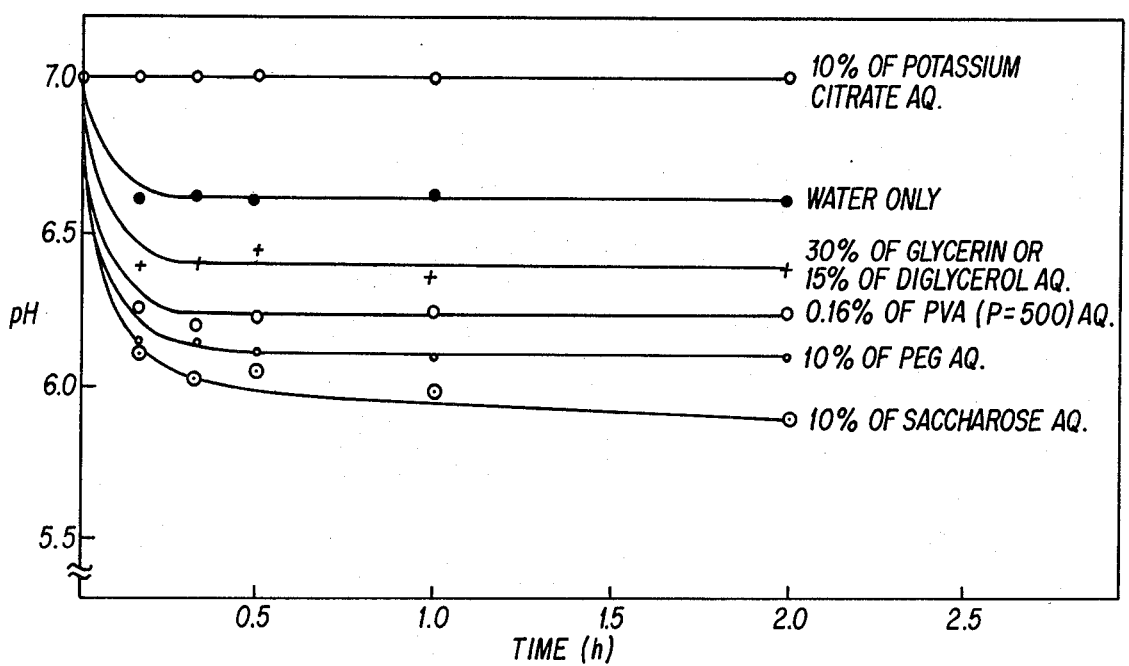
FIGS. 1-3 graphically represent the influence upon pH exerted by the addition of the water-soluble substances.
Figure 2:
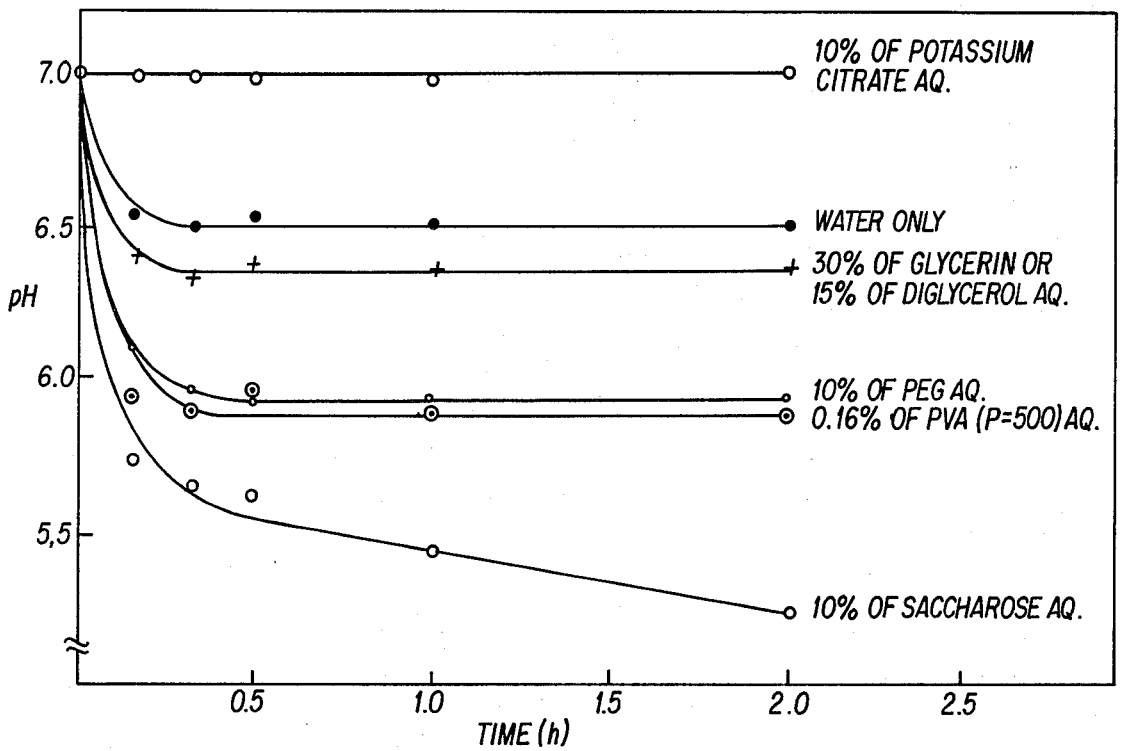
Figure 3:
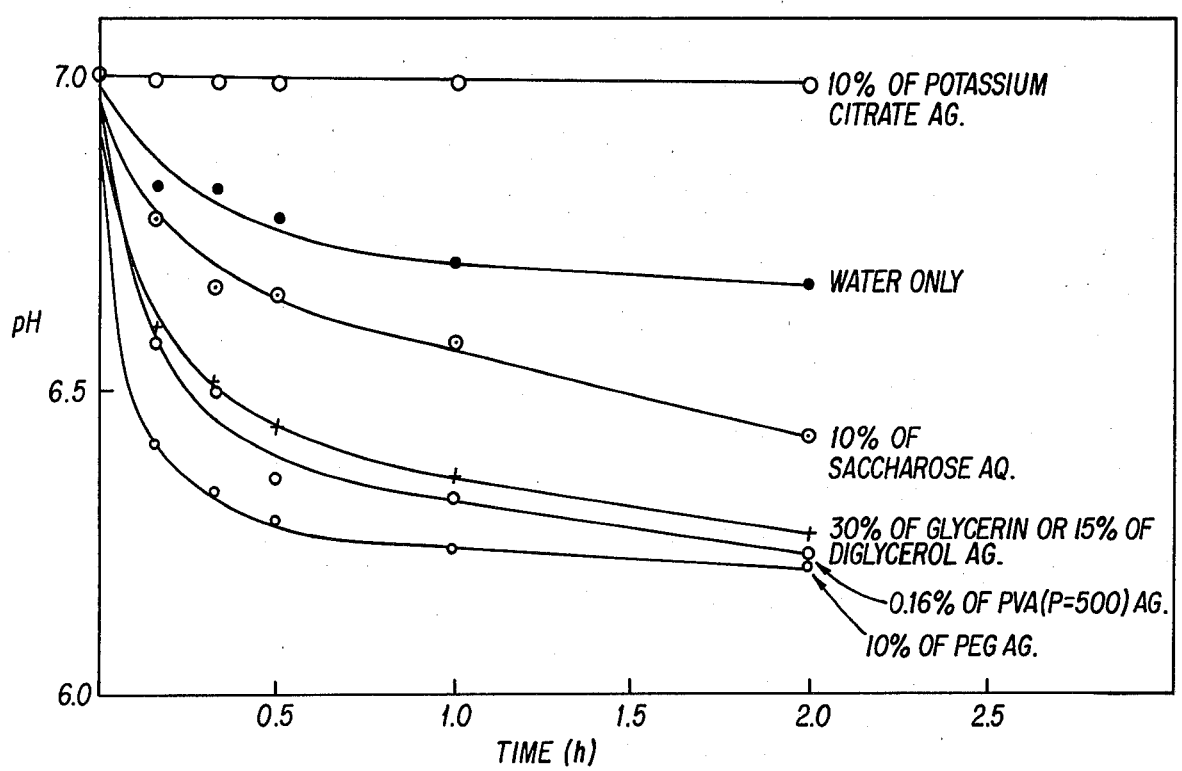

The invention covered by the said prior patent application is constituted by the method whereby dental caries activity is to be evaluated by means of color reaction upon variation in pH due to acids produced by culture of cariogenic bacteria. However, as a result of further subsequent studies, it has been discovered that acidity of dental plaque themselves is in correlation with the status praesens of dental caries. This means that it is possible to be readily informed of the status praesens of dental caries even without effectuating any cultivation of cariogenic bacteria and only by placing dental plaque in an aqueous solution containing coloring agents to make use of color reaction for observing any eventual variation in pH owing to the presence of acids in the sordes. In view of the fact, however, that the acids are present in dental plaque in a small amount and so pH of the evaluating solution can vary only in a very narrow range as shown in FIGS. 1-3 hereto appended, it constitutes a great difficulty to obtain a distinct color reaction and, at the same time, to make a choice of proper coloring agents. Under the circumstances, in order to render such a method practicable, the acid amount to be detected needs to be increased so as to widen the range of eventual variation in pH. On the other hand, a time-consuming method being not convenient as stated above, any other possible methods have been sought for. It has been confirmed thereupon that (1) a fairly sufficient amount of acids is present in cariogenic baterial cells and (2) these acids in the bacterial cells can be eluted by making use of osmotic pressure. Accordingly, combination of any agents producing an osmotic pressure which could elute the acids in bacterial cells with the evaluating solution should result in addition of the acids in dental plaque (namely extra-cellular acids) to the intra-cellular ones, and the acid amount contributing to color reaction will be increased, thus rendering the reaction more distinct. In addition, the said acid amount, reflecting most exactly the substantial amount which is present, has been found to be most advantageous for attaining the desired objects.

It is evident also from the foregoing that, according to this invention, additives intended for raising osmotic pressure are to be used. These additives have to be water-soluble substances capable of producing an osmotic pressure higher than the physiological one and, moreover, should display no buffer action so as to make color reaction distinct. Various water-soluble substances may be considered as satisfying such requisites, but polyvinyl alcohol, polythylene glycol, glycerin, diglycerol, saccharose, etc. may be mentioned as the typical ones. Besides, starch, agar-agar, gelatin, CMC, etc. also may be used. These substances may be utilized singly or in combination of more than two of them. The optimum concentration of the respective water-soluble substances in an aqueous solution varies according to the nature of these water-soluble substances, being in the range of 0.1–1% in case of polyvinyl alcohol, 5–50% in case of polyethylene glycol, 10–50% in case of glycerin, 5–50% in case of diglycerol and 5–50% in case of saccharose, for instance. In this connection, FIGS. 1–3 graphically represent the effect obtained with the addition of the said water-soluble substances to the evaluating solution, FIG. 1 showing relationship between pH of the test solution and time in the case where $5\times10^6$/ml of Streptococcus mutans KIR have been dispersed in 2 ml of the test solution, FIG. 2 in the case where $5\times10^9$/ml of Lactobacillus casei have been dispersed in the test solution and FIG. 3 in the case wherein 0.02 ml of a suspension in physiological saline solution of dental plaque collected from the patient's oral cavity has been added to the test solution. It is evident from these figures that, whereas the range of variation in pH is narrow in case of a solution in simple pure water, pH considerably lower than the initial one is obtained by using a test solution to which water-soluble substances raising osmotic pressure have been added. These tendencies have been found to be approximately identical both with the use of bacterial cells only (FIGS. 1 and 2) and with that of dental plaque containing the bacterial cells (FIG. 3). But, the use of a substance having buffer action like potassium citrate does not enable the objects of this invention to be attained because of pH of the test solution no longer varying.

In consequence, when proper coloring agents have been combined with this test solution, it is possible to evaluate the status prasens of dental caries accurately and within a short time by means of color reaction. No special limitation is placed on the coloring agents to be used, provided that they can give different colors at pH in the range of 7.5–5.0 and undergo no alteration in coloring properties during storage. As the typical ones, bromothymol blue, methyl red, China blue, alizarin blue, etc. may be cited, which may be used singly or in combination of more than two of them. By the way, it is effective also to make an attempt at quality control by adding an antibiotic (Chloramphenicol, etc.) or antiseptic (sodium azide, etc.) to the test solution so that it may not be made rotten during storage.

The test solutions most preferable from the viewpoint of these points put altogether are to be of composition as shown hereunder for instance, the respective pH values for coloration and colors to be exhibited being stated in addition.

| (1) | Polyethylene glycol (mean molecular weight: 400) | 10% in weight |
| --- | --- | --- |
| | Sodium azide | 0.03% in weight |
| | Bromothymol blue | 0.005% in weight |
| | Purified water | rest |
| | pH (adjusted with 0.1 N—NaOH) | 7.2 |
| | At pH 7.2: blue | At pH 6.6: green |
| | At pH 6.0: yellowish green | At pH 5.4: yellow |
| (2) | Polyvinyl alcohol (P = 500) | 0.16% in weight |
| | Sodium azide | 0.03% in weight |
| | Bromothymol blue | 0.005% in weight |
| | Methyl red | 0.003% in weight |
| | Purified water | rest |
| | pH (adjusted with 0.1 N—NaOH) | 7.2 |
| | Al pH 7.2: blue | At pH 6.6: yellowish green |
| | At pH 6.0: yellow | At pH 5.4: reddish orange |
| (3) | Saccharose | 10% in weight |
| | Chloramphenicol | 0.0005% in weight |
| | Alizarin blue | 0.003% in weight |
| | China blue | 0.001% in weight |
| | Purified water | rest |
| | pH (adjusted with 0.1 N—NaOH) | 7.2 |
| | At pH 7.2: green | At pH 6.6: yellowish green |
| | At pH 6.0: light yellow | At pH 5.4: blue |

These 3 kinds of test solution being exemplified above merely as the typical ones, what is essential is that (1) the aqueous solution contains water-soluble substances capable of raising osmotic pressure and not participating by themselves in color reaction, yet having no buffer action, and (2) the solution contains at the same time coloring agents giving distinct colors at pH in the above-stated range. Provided these requisites are satisfied, the kinds of the water-soluble substances and the coloring agents and their amount to be added or their combination may be appropriately changed at discretion.

It has been stated in the foregoing that, according to this invention, dental caries activity can be accurately evaluated by means of distinct color reaction to be caused by eluating intra-cellular acid components of cariogenic bacteria forcefully by osmosis with the use of an aqueous solution containing the specific water-soluble substances. But, since dental plaque also comprise a fairly sufficient amount of acids in addition to the intra-cellular acid components of cariogenic bacteria, pH can be somewhat lowered also by extra-cellular acids even with he use of pure water (containing no water-soluble substances), as shown in FIGS. 1–3. Accordingly, it is possible also to evaluate dental caries activity by means of color reaction due to the extra-cellular acid components with the use of pure water only, as a simplified method. In particular, the said simplified method will be of more practicability with the use of coloring agents sensitive enough in giving colors upon slight variation in pH with an increase in amount to be added of dental plaque for making the amount of acid components more larger. However, it is recommended in case of adoption of the said simplified method to adjust pH of the aqueous solution at higher than 7 and to utilize coloring agents capable of giving different colors at pH in the range of 7.2–5.8 so as to give rise to a great variation in pH with a small amount of acid components, or to increase the amount to be added of dental plaque for the same purpose.

Now, the finding obtained from clinical investigation on the compositions according to this invention as well as the results of examination of the correlation existing between the invention of the said prior patent application and the present one are going to be stated in the following lines.

Clinical Trial Example

Sordes on teeth which had been collected by means of a cotton applicator from the oral cavity of each of the subjects consisting of 50 infants were put in 1 ml of the said test solution (1) and homogeneously dispersed. pH having been measured 30 minutes after, the status praesens of dental caries was evaluated on the basis of coloration of the solution (Table 1). Then, the results of this evaluation was compared with the seriousness indices obtained from actual examination of the oral cavity (Table 2). The findings are shown in Table 3.

TABLE 1

| Color reaction and evaluation criterion | |
|---|---|
| Coloration | Evaluation |
| Yellow | +++ |
| Yellowish green | ++ |
| Green | + |
| Blue | − |

TABLE 2

| Calculation of seriousness index of dental caries | | |
|---|---|---|
| | Score | |
| Healthy tooth | 0 | Dental caries seriousness index |
| C1. C2, C" | 1 | |
| C3, C4 | 2 | $= \dfrac{\text{Total score}}{2 \times \text{total erupted teeth}} \times 100$ |
| Repaired tooth, Co | 0.5 | |

TABLE 3

| Dental caries seriousness index | pH of test solution | Evaluation |
|---|---|---|
| 1.3 | 6.0 | ++ |
| 7.5 | 5.7 | ++ |
| 5.0 | 6.0 | ++ |
| 12.5 | 5.2 | +++ |
| 2.5 | 6.1 | + |
| 15.0 | 5.4 | +++ |
| 10.0 | 5.3 | +++ |
| 7.5 | 5.9 | ++ |
| 5.0 | 5.5 | ++ |
| 5.0 | 6.0 | ++ |
| 7.5 | 5.6 | ++ |
| 11.3 | 5.2 | +++ |
| 4.7 | 6.1 | + |
| 11.25 | 5.4 | +++ |
| 16.30 | 5.1 | +++ |
| 0 { (21 subjects) | 7.2~6.7 | − |
|    (14 subjects) | 6.6~6.1 | + |

It is evident from Table 3 that there exists an obvious correlation between the dental caries seriousness indices obtained upon actual examination of the oral cavity and the results of evaluation as well as pH values obtained with the use of the compositions according to this invention. By using the compositions according to this invention, therefore, it is possible to evaluate accurately the status praesens of dental caries by means of color reaction and without actual examination of the oral cavity.

Correlation with the invention of the prior patent application

Comparative experiments were carried out on 60 infants with a view to inquiring into possible correlation between the evaluations made with the use of the compositions according to this invention and those whth the use of the compositions according to the invention of the prior patent application (Public Disclosure of Patent Application No. 1589/75). Namely, the evaluations given after bacterial cultivation for 48 hours with the use of the composition described in Table 4 (according to the invention of the prior patent application) were compared with the evaluations obtained with the said composition (1) (according to the present invention) so as to examine possible correlation between both of these compositions. (However, the comparison was performed in terms of pH of the respective evaluating solutions so that more accurate correlationship may be observed.)

TABLE 4

| Composition according to the invention of the prior patent application | |
|---|---|
| Saccharose | 20% in weight |
| Tryptose (an amino acid composite prepared by Difco in U.S.A.) | 1.8% in weight |
| Sodium chloride | 0.6% in weight |
| Sodium azide | 0.03% in weight |
| Bromocresol green | 0.001% in weight |
| Bromocresol purple | 0.002% in weight |
| Distilled water | rest |

Figure 4:
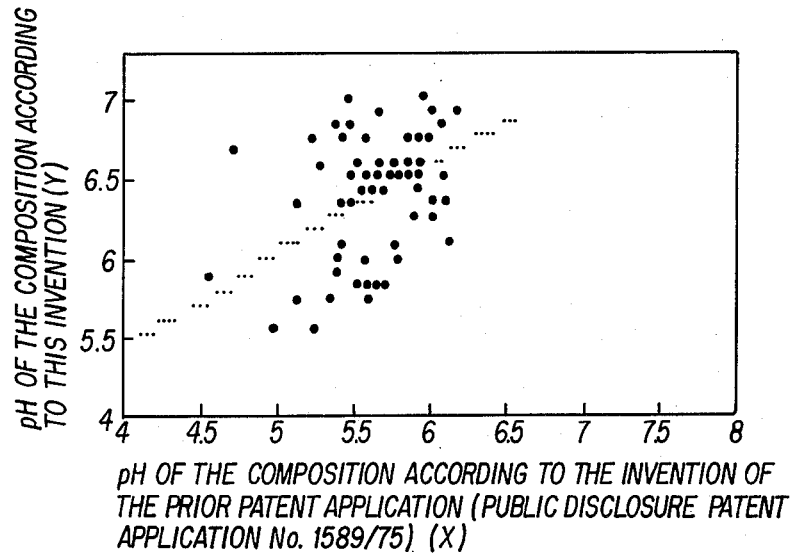
FIG. 4 is a graphic diagram showing correlation between the evaluations with the use of the composition according to the invention of the prior patent application and those with the use of the compositions according to this invention.

As a result thereof, the relation as represented in FIG. 4 was confirmed. Besides, when a regression equation of $Y = 3.0143 + 0.5972X$ was set up with the pH in case of the use of the composition according to the invention of the prior patent application (X) and the pH in case of the use of the composition according to this invention (Y) on the basis of the results shown in FIG. 4, a regression coefficient of $\gamma = 0.568$ was obtained which confirmed the existence of a definite correlationship. Analysis of the 4-grade criterion for evaluation with the composition according to the invention of the prior patent application by applying it to the said regression equation gave the results as shown in Table 5.

TABLE 5

| | Evaluation criteria | | | |
|---|---|---|---|---|
| | Composition according to the invention of the prior patent application | | Composition according to this invention | |
| Evaluation | pH | Coloration | pH | Coloration |
| +++ | 4.0 | Yellow | 5.4 | Yellow |
| ++ | 5.0 | Yellowish green | 6.0 | Yellowish green |
| + | 6.0 | Green | 6.6 | Green |
| − | 7.0 | Blue | 7.2 | Blue |

As seen clearly from these comparative experiments, by using the composition according to this invention, dental caries activity can be evaluated with an accuracy of the same degree as that with the composition according to the invention of the prior patent application without any cultivation of cariogenic bacteria but only by percolating intra-cellular acids from the bacteria.

This invention is constituted as described in the foregoing, according to which, quite unlike the prior methods where-by cultivation of cariogenic bacteria is indispensable, it is possible to evaluate accurately the status praesens of dental caries and its activity within a very short time by making use of percolation of intra-cellular acids of cariogenic bacteria. In addition, the method according to this invention whereby color reaction is utilized and so the operation for evaluation is simplified is of a great practical advantage in offering the compositions for diagnosis of dental caries activity that can replace actual examination of the oral cavity.

What is claimed is:

1. Compositions for diagnosis of dental caries activity consisting essentially of: an aqueous solution of water-soluble substances selected from the group consisting of polyvinyl alcohol and polyethylene glycol, said water-soluble substances being present in an amount effective to produce an osmotic pressure higher than the physiological one on the cell membrane of cariogenic bacteria present in dental plaque, and yet free from any buffer action by themselves; and at least one coloring agent giving different colors at pH in the range of 7.5–5.0.

2. Compositions according to claim 1 in which the water-soluble substance is polyvinyl alcohol and its concentration in said aqueous solution is 0.1–1%.

3. Compositions according to claim 1, in which the water-soluble substance is polyethylene glycol and its concentration in said aqueous solution is 5–50%.

4. Compositions according to claim 1, in which said at least one coloring agent is bromothymol blue, methyl red, China blue or alizarin blue.

5. Compositions for diagnosis of dental caries activity consisting essentially of: an aqueous solution of water-soluble substances selected from the group consisting of polyvinyl alcohol and polyethylene glycol, said water-soluble substances being present in an amount effective to produce an osmotic pressure higher than the physiological one on the cell membrane of cariogenic bacteria present in dental plaque, and yet free from any buffer action by themselves; an antibiotic and/or antiseptic combined with the aqueous solution containing the water-soluble substances; and at least one coloring agent giving different colors at pH in the range of 7.5–5.0.

6. A method for the diagnosis of dental caries activity, comprising introducing dental plaque into the composition of claim 1, and measuring the pH of the resultant mixture, wherein decreased pH values are indicative of increased dental caries activity.

* * * * *